United States Patent [19]
Miller, Jr. et al.

[11] 3,936,503
[45] Feb. 3, 1976

[54] ARYL-SUBSTITUTED ALIPHATIC DIQUATERNARY COMPOUNDS

[75] Inventors: Eugene J. Miller, Jr., Wheaton; Harlan E. Tiefenthal, Western Springs, both of Ill.

[73] Assignee: Akzona Incorporated, Asheville, N.C.

[22] Filed: Apr. 9, 1970

[21] Appl. No.: 27,161

Related U.S. Application Data

[63] Continuation-in-part of Ser. No. 731,695, May 24, 1968, abandoned, which is a continuation-in-part of Ser. No. 502,563, Oct. 22, 1965, abandoned.

[52] U.S. Cl....... 260/567.6 P; 260/501.15; 252/8.6; 252/8.9
[51] Int. Cl.².......................................... C07C 87/30

[58] Field of Search ................. 260/567.6 P, 501.15

[56] References Cited
UNITED STATES PATENTS
3,055,939  9/1962  Cavallito et al. ............. 260/567.6 P

*Primary Examiner*—James O. Thomas, Jr.
*Assistant Examiner*—James H. Reamer
*Attorney, Agent, or Firm*—Francis W. Young

[57] ABSTRACT

Aryl-substituted aliphatic diquaternary ammonium compounds having a long chain alkyl group in which an aryl group is attached to an internal carbon atom and the nitrogen atoms are connected by an alkylene group, useful as cationic bituminous emulsifiers and for fabric treating and textile processing.

17 Claims, No Drawings

ARYL-SUBSTITUTED ALIPHATIC DIQUATERNARY COMPOUNDS

CROSS-REFERENCE TO RELATED APPLICATION

This application is a continuation-in-part of our copending application Ser. No. 731,695, now abandoned filed May 24, 1968 as a continuation-in-part of our application Ser. No. 502,563, filed Oct. 22, 1965, and now abandoned.

This invention relates to a novel class of aryl-substituted aliphatic diquaternary compounds, and more particularly this invention relates to diquaternary compounds containing one long chain aliphatic group to which an aryl group is attached to an internal carbon atom, thereby providing an aralkyl group. The compounds of this invention have utility as cationic emulsifiers for preparing asphalt or other bituminous emulsions. The compounds may also be used for other purposes, such as for fabric treatment and in textile processing.

The diquaternary compounds of the present invention can be represented by the following structural formula:

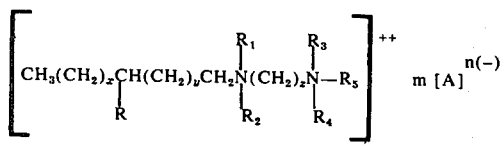

wherein $R_1$ and $R_5$ are selected from the group consisting of alkyl radicals having from 1 to 3 carbon atoms; $R_2$ is selected from the group consisting of alkyl radicals having from 1 to 3 carbon atoms, $-(CH_2CH_2O)_pH$, and

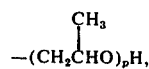

$R_3$ is selected from the group consisting of alkyl radicals having from 1 to 3 carbon atoms, $-(CH_2CH_2O)_wH$, and

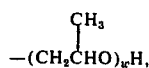

$R_4$ is selected from the group consisting of alkyl radicals having from 1 to 3 carbon atoms, $-(CH_2CH_2O)_rH$, and

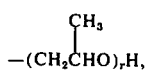

wherein $p$, $r$ and $w$ are integers from 1 to 40 and the sum of $p$, $r$, and $w$ is less than 80; R is selected from phenyl, naphthyl, and phenyl-substituted with from 1 to 2 groups selected from methyl, hydroxy, and methoxy; $x$ is an integer from 0 to 18; $y$ is an integer from 1 to 19 and the sum of $x$ and $y$ is an integer from 8 to 19; $z$ is an integer from 2 to 6; A is an anion; $m$ and $n$ are integers from 1 to 2 and the product of $n$ times $m$ is 2; said compounds comprising isomeric mixtures with respect to the position of attachment of R to the alkyl chain.

In one subclass, $R_1$, $R_2$, $R_3$, $R_4$ and $R_5$ are methyl, and $z$ is 3. In another subclass, $R_1$ and $R_5$ are methyl, $R_2$ is $-]CH_2CH_2O)_pH$, $R_3$ is $-(CH_2CH_2O)_rH$, and $R_4$ is $-(CH_2CH_2O)_wH$, with $p$, $r$ and $w$ being integers of 1 to 20, and with the total of $p$, $r$, and $w$ not exceeding 50, and $z$ is 3. In a preferred subclass $p$, $r$ and $w$ are integers of 1 to 5 with the total of $p$, $r$ and $w$ of 3 to 15. In another preferred subclass $p$, $r$ and $w$ are 1 with the total of $p$, $r$ and $w$ being 3, forming β-hydroxyethyl groups. In these subclasses, the other variables have the meanings previously defined, and in particularly preferred subclasses R is phenyl, $n$ is 1, $m$ is 2, and A is chloride.

In another subclass, $R_2$ is

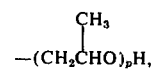

$R_3$ is

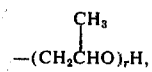

and $R_4$ is

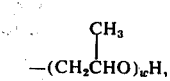

with $p$, $r$ and $w$ being integers of 1 to 20 and with the total of $p$, $r$ and $w$ not exceeding 50. In a preferred subclass $p$, $r$ and $w$ are integers of 1 to 5 with the total of $p$, $r$ and $w$ of 3 to 15. In another preferred subclass $p$, $r$ and $w$ are 1 with the total of $p$, $r$ and $w$ being 3, forming β-hydroxypropyl groups. The other variables have the meanings previously defined, and in particularly preferred subclasses R is phenyl, $m$ is 2, $n$ is 1, and A is chloride.

The ethoxylated and propoxylated diquaternary ammonium compounds of our invention are produced from ethoxylated and propoxylated diamines which may be produced according to the teachings more fully disclosed in our copending application Ser. No. 590,474 filed Oct. 31, 1966, now U.S. Pat. No. 3,492,352. Alkoxylated amines are well known in the art to be produced by the reaction of an alkylene oxide such as ethylene oxide or propylene oxide with a primary or secondary amine. The use of several moles of alkylene oxide per mole of amine results in an alkylene oxide adduct having repeated ether linkages with a terminal hydroxy function. The random growth of an alkylene oxide adduct by addition of alkylene oxide to hydroxyl functions is well known in the art. Therefore, when more than three moles of alkylene oxide is reacted with a diamine a mixture of alkylene oxide adduct chain lengths is formed. The product thus formed is identified by the sum of the alkylene oxide units or the moles of alkylene oxide reacted with a mole of amine. Thus, $p$, $r$ and $w$ in the above formulae are integers such that the alkoxylated amines contain from 1 to 40 moles of alkylene oxide per amino function. In the above formulae, $w$, $r$, and $p$ are integers having a sum of 1 to 80. Amines containing the beta hydroxyethyl function attached directly to the nitrogen atom have been found especially suitable to form the compounds for use in this invention.

It will be noted from the foregoing formula that the diquaternary compounds contain at least one long chain aryl-substituted aliphatic group, or, more specifically, an arylalkyl group. In one specific embodiment the alkyl portion of the arylalkyl group contains a total of 18 carbons, with $x$ and $y$ totalling 15. In other specific embodiments, the alkyl portion of the arylalkyl groups contain 11, 16 or 22 carbons. More generally, the total of $x$ and $y$, which is three less than the total of carbons in the alkyl chain of the arylalkyl, may range from 8 to 19. In one especially preferred subclass of compounds $x$ is an integer of 0 to 14, $y$ is an integer of 1 to 15, the total of $x$ and $y$ being 15, as for example derived by arylation of oleic acid. In another preferred subclass of compounds $x$ is an integer of 0 to 8, $y$ is an integer of 1 to 8, the total of $x$ and $y$ being 8, as for example derived by arylation of undecylenic acid. In another preferred subclass of compounds $x$ is an integer of 0 to 19, $y$ is an integer of 1 to 19, the total of $x$ and $y$ being 19, as for example derived by arylation of erucic acid.

The compounds also contain at least two, or up to five, short chain alkyl groups which are bonded to the nitrogen atoms. While methyl groups are preferred, the alkyl groups may also comprise ethyl or propyl or mixtures of methyl, ethyl, or propyl.

In the formula, R represents the aryl substituent. The carbon to which the aryl group is attached varies with the respective values of $x$ and $y$. With unsaturated alkenyl chains, such as oleyl, under most reaction conditions the double bond migrates up and down the chain (isomerization by hydrogen ion transfer), resulting in a mixture of isomeric products. In arylating oleyl, there is a tendency for the $C_8$-$C_{14}$ and the $C_{17}$ aryl isomers to predominate, but smaller mole percentages of other isomers, such as the $C_6$, $C_7$, $C_{15}$ and $C_{16}$ isomers are also produced. The mole percent of the $C_2$-$C_5$ isomers is usually quite small. The relative proportions of the various isomers may vary depending on the arylation process. See J. Org. Chem. 30, 885–888 (1965). However, the total of $x$ and $y$ will remain constant for the particular unsaturated chain, viz., 15, for oleyl, 8 for undecyl, 19 for behenyl, etc. By arylation, oleic acid is converted to aryl-substituted stearic acid, Similarly, palmitoleic, erucic, and 10-undecenoic acids can be converted to the corresponding aryl-substituted carboxylic acids. Ordinary commercial grade oleic acid contains several percent of palmitoleic acid, and therefore a mixture of aryl-substituted stearic and palmitic acids are obtained by arylation.

Among the preferred aryl substituents are phenyl, hydroxyphenyl, tolyl, anisyl, and naphthyl. More generally, the phenyl nucleus may be substituted with 1 or 2 groups such as methyl, hydroxy, and methoxy. Other groups coming within this subclass are cresyl, resorcyl, xylyl, etc.

Since the diquaternaries are in the form of salts, the cationic portion of the molecule will be associated with an anionic portion. The particular anion is not critical, and generally the anion may be any of those which are commonly present in quaternary compounds, such as monovalent or divalent anions. To provide for complete neutralization, the formula indicates that $m$ will be 2 for monovalent anions where $n$ is 1, and 1 for divalent anions where $n$ is 2. The halogen salts chloride, bromide and iodide of the diquaternary are particularly useful. Chloride salts of the diquaternary are particularly desirable where the compounds are to be employed as cationic emulsifiers, but other salts can be used such as hydroxides, sulfates, nitrates, hydrochlorates, perchlorates, hypochlorates, formates, acetates, etc. For certain purposes, the anion should be selected to provide water solubility or water dispersibility.

The diquaternary ammonium compounds contain an alkylene group linking the two nitrogen atoms. The alkylene group may contain from 2 to 6 carbon atoms; that is the alkylene group may be dimethylene, trimethylene, tetramethylene, pentamethylene or hexamethylene and their branched chain isomers such as 2-methyl-1, 3-propylene, 1-methyl-1, 3-propylene and 1-methyl ethylene. One especially preferred embodiment is the presence of the trimethylene group wherein $z$ is 3.

The diquaternary compounds of our invention may be obtained by different process routes to obtain the diamine from which the diquaternary is formed. N-arylalkyl alkylene diamines may be obtained from initial reactants of either unsaturated aliphatic acid or unsaturated aliphatic alcohol.

Unsaturated aliphatic carboxylic acids are the desired initial reactant to produce n-arylalkyl trimethylene diamines. The unsaturated aliphatic acid is preferably converted to the nitrile derivative, which is reacted with an arylating agent in the presence of a catalyst such as aluminum chloride. The arylalkyl nitrile compound, by procedures well known in the art, can then be converted to the corresponding aliphatic amine by hydrogenation. The primary amine can then be cyanoethylated by reaction with acrylonitrile to obtain the cyanoethyl arylalkyl amine, which can then be converted to the diamine by hydrogenation, resulting in N-arylalkyl trimethylene diamine.

The unsaturated aliphatic acid may be first arylated and then converted to the primary amine through the nitrile. For direct arylation of fatty acids, catalysts other than aluminum chloride are preferred, such as activated clays, or hydrofluoric acid. A process employing hydrofluoric acid as the catalyst is described in U.S. Pat. No. 2,275,312, while the use of an activated clay is described in U.S. Pat. No. 3,074,983. An improved hydrofluoric acid process is described and claimed in copending application, Ser. No. 679,251, filed Oct. 30, 1967, entitled "Process for Mono-Alkylation of Aromatic Compounds". The arylated fatty acid can then be used to prepare the diquaternary compounds of the present invention. For example, phenylstearic acid, or other aryl-substituted long chain aliphatic acid can be converted to the corresponding nitrile, the nitrile converted to the primary amine, and the primary amine converted to the diamine.

The N-arylalkyl alkylene diamine may also be obtained by arylating an unsaturated alcohol, such as oleyl alcohol to form 9(10)-phenylstearyl alcohol. The aryl-alkyl alcohol can be readily converted to the arylalkyl bromide, chloride or iodide by bubbling gaseous hydrogen halide through the alcohol at a temperature of from 50° to 150°C. Essentially quantitative conversion is obtained. The arylalkyl bromide, chloride, or iodide is then reacted with an excess of alkylene diamine, having from 2 to 6 carbon atoms, preferably in an alcohol solvent at reflux temperatures. The alcohol solvent may be removed by distillation and the excess alkylene diamine reactant separates from the product N-arylalkyl alkylene diamine. The product may be purified by solvent extraction and water washing. Further exemplification of this process using ethylene diamine is shown in Journal of American Chemical Society, 67, 1581 (1945). Preferred compounds produced according to this method include N-arylalkyl dimethylene diquaternary ammonium compounds and the arylalkyl hexamethylene diquaternary ammonium compounds.

The diamines produced by any of these methods can then be quaternized by reaction with a suitable quaternizing agent such as methyl chloride or dimethyl sulfate. The diamine can also be ethoxylated by reaction with ethylene oxide, or propoxylated with propylene oxide, before being quaternized. It will be understood that such procedures are well known in the art.

This invention is further illustrated by the following specific examples.

EXAMPLE I

Phenylstearic acid and hydroxyphenylstearic acid were prepared from commercial grade oleic acid which contained a few percent of palmitoleic acid by a Friedel-Crafts reaction using aluminum chloride as the catalyst, and benzene and phenol, respectively, as the arylating agents. Thereafter, phenyloctadecylnitrile was prepared on a continuous nitrile unit over bauxite catalyst at 280°–300°C from 1127 grams phenylstearic acid. A crude yield of 833.5 grams of phenyloctadecylnitrile was obtained. The product was a mixture of isomers, predominately the $C_8$ to $C_{14}$ and the $C_{17}$ isomers with lesser proportions of other isomers. Similarly, hydroxyphenyloctadecylnitrile was obtained in 62 percent crude yield from the crude acid.

EXAMPLE II

Phenyloctadecylnitrile (591 grams), prepared as described in Example I, was reduced in a 1-liter, Parr autoclave over 2 percent alcohol washed Raney nickel catalyst in the presence of ammonia (150 psi/3-0°–40°C.) and hydrogen (800 psi total pressure at 125°C for 4–5 hours). The product was obtained as a light amber oil, 582.3 grams (97% crude yield). Pure phenyloctadecylamine was obtained in 67 percent yield upon distillation at 183°–190°/0.3 mm. Similarly, hydroxyphenyloctadecylamine was prepared in 91.5 percent crude yield and 81 percent distilled yield from distilled hydroxyphenyloctadecylnitrile prepared as in Example I.

EXAMPLE III

N-(Beta-cyanoethyl)phenyloctadecylamine was prepared as follows: Acrylonitrile (61.0 grams, 1.15 moles) was added slowly over 2 hours, with stirring, to a mixture of phenyloctadecylamine, prepared as described in Example II, (363.8 grams, 1.05 moles) and 17.0 grams water at 60°–70°C. The resulting mixture was then stirred at 70°–80° for 4 additional hours. The water was separated and the product dried under reduced pressure at 60°–70°C.

Analysis: NE = 401 (calc'd 398.6);
PA = nil;
SA = 99.5%.

N-(Beta-cyanoethyl)hydroxyphenyloctadecylamine was prepared by the same procedure and resulted in a product with the following analysis:
PA = 0.04 meg/g.
SA = 82%
TA = 14.2% (456 Mol. Wt. HClO$_4$ titration)
IRNo. P5032-3 % CN = 100.4

EXAMPLE IV

N-(Beta-cyanoethyl)phenyloctadecylamine prepared as described in Example III was reduced in the presence of 1 percent alcohol washed Raney nickel, ammonia (125 psi/40°C.) and hydrogen (800 psi total pressure) at 135° in 6–7 hours, thereby obtaining phenyloctadecyltrimethylene diamine. The product was a mixture of isomers, predominately the $C_8$ to $C_{14}$ and $C_{17}$ isomers, with lesser proportions of other isomers.

Analysis: NE = 201 (Calc'd. 201.3);
PA = 53.4%;
SA = 45.5%;

Reduction of the N-(Beta-cyanoethyl)hydroxyphenyloctadecylamine of Example III under similar conditions yielded hydroxyphenyloctadecyltrimethylene diamine with the following analysis:
NE = 225.5 (Calc'd. 209.3)
PA = 48.3%
SA = 34.5%
TA = 7.5%

EXAMPLE V

Phenyloctadecyltrimethylene diamine (50 grams, 0.124 mole) prepared as described in Example IV was quaternized in isopropanol and sodium bicarbonate (35.3 grams, 0.372 mole) with methyl chloride at 80°–90°/65–70 psi for 4–5 hours with periodic venting. The sodium bicarbonate was removed by filtration and the solvent stripped under reduced pressure to yield 60 grams of a viscous oil.

Analysis: 88.1% diquaternary;
2.1% free amine.

The product N,N,N',N',N'-pentamethyl-N-phenyloctadecyltrimethylene diammonium dichloride, was a mixture of isomers, predominately the $C_8$ to $C_{14}$ and the $C_{17}$ isomers. The hydroxyphenyloctadecyltrimethylene diamine of Example IV can be similarly quaternized.

EXAMPLE VI

A 500 ml. glass reactor was charged with 74 grams (0.178 mole) of N-(Gamma-aminopropyl)tolyloctadecylamine, 49.0 grams (0.59 mole) of sodium bicarbonate and 150 ml. of isopropanol. The reaction mixture was heated to 60°–70°C. and gaseous methyl chloride added to a pressure of 60–70 psig. The mixture was maintained at 60°–70°C/60–70 psig for 5 hours with periodic venting. Sodium chloride and excess sodium bicarbonate were removed by filtration. The isopropanol solution of N,N,N',N',N'-pentamethyl-N-(tolyloctadecyl) trimethylenediammonium dichloride had the following analysis:

| | |
|---|---|
| Diquaternary | 41.8% |
| Free amine | 4.05% |
| Amine · HCl | 0.18% |

EXAMPLE VII

Similarly, N-(Gamma-aminopropyl)anisyloctadecylamine (69.0 grams, 0.16 mole) in isopropanol (200 ml) was quaternized with methyl chloride at 60°–70°C/60–70 psig in 5 hours with periodic venting in the presence of sodium bicarbonate (39.5 grams, 0.483 mole). The isopropanol solution of N,N,N',N',-N'-pentamethyl-N-(anisyloctadecyl)trimethylenediammonium dichloride had the following analysis:

| | |
|---|---|
| Diquaternary | 49.9% |
| Free amine | 0.59% |
| Amine · HCl | 0.27% |

EXAMPLE VIII

In like manner, N-(Gamma-aminopropyl)naphthyloctadecylamine (15 grams, 0.032 mole) was quaternized in isopropanol (150 ml) with methyl chloride 60°–70°C/60–70 psig in 5 hours with periodic venting in the presence of sodium bicarbonate (8.1 grams, 0.097 mole). The isopropanol solution of N,N,N',N',-N'-pentamethyl-N-(naphthyloctadecyl)trimethylenediammonium dichloride had the following analysis:

| | |
|---|---|
| Diquaternary | 14 % |
| Free amine | 0.4% |
| Amine · HCl | Nil |

EXAMPLE IX

A 500 ml glass reactor was charged with 82.6 grams (0.175 mole, 0.35 equiv.) of N-(Gamma-aminopropyl)xylyloctadecylamine, 89.1 grams (1.06 moles) of sodium bicarbonate and 150 ml of isopropanol. The reaction mixture was heated to 80°C and gaseous methyl chloride introduced at 85 psig. The mixture was maintained at 80°–85°C/85–90 psig for 4 hours with periodic venting. Sodium chloride and excess sodium bicarbonate were removed by filtration. The isopropanol solution of N,N,N',N',N'-pentamethyl-N-(xylyloctadecyl)trimethylenediammonium dichloride had the following analysis:

| | |
|---|---|
| Diquaternary | 44.2 % |
| Free amine | 0.38% |
| Amine · Hcl | Nil |

EXAMPLE X

N-(Gamma-aminopropyl)phenyldocosylamine (25.5 grams, 0.05 mole, 0.055 equiv.) in isopropanol (about 150 ml) was quaternized with methyl chloride at 70°–75°C/70–80 psig in 2.5 hours in the presence of sodium bicarbonate (13.4 grams, 0.16 mole) with periodic venting. The isopropanol solution of N,N,N',N',-N'-pentamethyl-N-(phenyldocosyl)trimethylenediammonium dichloride had the following analysis:

| | |
|---|---|
| Diquaternary | 27.1 % |
| Free amine | 0.23% |
| Amine · HCl | Nil |

EXAMPLE XI

A 500 ml glass reactor was charged with 78.6 grams (0.25 mole) of N,N',N'-tri(Beta-hydroxyethyl)-N-(xylyloctadecyl)trimethylene diamine and about 120 ml of isopropanol. The mixture was heated to 80°C and gaseous methyl chloride was introduced at 85 psig. The mixture was maintained at 80°–85°C/85–90 psig for 10 hours. The isopropanol solution of the diquaternary ammonium salt had the following analysis:

| | |
|---|---|
| Diquaternary | 38.8 % |
| Free amine | 0.07% |
| Amine · HCl | 0.96% |

EXAMPLE XII

A 500 ml glass reactor was charged with 51.5 grams (0.087 mole, 0.175 equivalent) of the reaction product of 5 moles of propylene oxide with N-(Gamma-aminopropyl)phenylundecylamine (neutralization equivalent, N.E.295, tertiary amine 100%), and 80 ml of iospropanol. The reactant diamine contained two tertiary nitrogen atoms showing the substitution of the β-hydroxypropyl groups for all of the active amino hydrogens. Further adduct formation using the remaining 2 moles of propylene oxide occurred on a statistical basis as is well known by those skilled in the art. The reactor was sealed and the mixture heated to 80°C. Gaseous methyl chloride was introduced at 80 psig and the reaction mixture maintained at 80°–85°C/75–80 psig for three hours. The temperature was then raised to 100°C at 80–85 psig and maintained at 100°–105°C/-80–85 psig for an additional 16 hours. The diquaternary salt was obtained as an iospropanol solution having the following analysis:

| | |
|---|---|
| Diquaternary | 35.8% |
| Free amine | Nil |
| Amine · HCl | 5.1% |

EXAMPLE XIII

A 250 ml glass reactor was charged with 72.0 grams (0.09 mole, 0.18 equivalent) of the reaction product of 7.4 moles ethylene oxide with N-(Gamma-aminopropyl)phenyldocosylamine (N.E. 400, tertiary amine 96.6%), 104 ml of isopropanol and 2.0 grams (2.5% by wt.) of sodium bicarbonate. The reactant diamine contained 96.6% tertiary amine having substantially complete substitution of β-hydroxyethyl groups for all of the active amino hydrogens. Further adduct formation using the remaining 4.4 moles of ethylene oxide took place on a statistical basis as is well known by one skilled in the art. The reactor was sealed and the mixture heated to 80°C. Gaseous methyl chloride was introduced at 70 psig and the reaction mixture maintained at 80°–85°C/70–80 psig for about 10 hours. Sodium chloride and excess sodium bicarbonate were removed by filtration and the diquaternary product obtained as an isopropanol solution having the following analysis:

| | |
|---|---|
| Diquaternary | 54.5% |
| Free amine | 2.74% |
| Amine · HCl | Nil |

EXAMPLE XIV

A 250 ml glass reactor was charged with 49.0 grams (0.102 moles) off the reaction product of 4 moles of ethylene oxide with N-(Gamma-aminopropyl)-phenylundecylamine (N.E. 240, tertiary amine 99.9%), 50 ml of isopropanol and 2.5 grams (5% by wt.) of sodium bicarbonate. The reactor was sealed and the mixture heated to 80°C. Gaseous methyl chloride was introduced at 60 psig and the reaction mixture maintained at 80°–85°C/60–65 psig for 7 hours. Sodium chloride and excess sodium bicarbonate were removed by filtration. The diquaternary product was obtained as an isopropanol solution having the following analysis:

| | |
|---|---|
| Diquaternary | 46.0% |
| Free amine | 1.17% |
| Amine · HCl | Nil |

EXAMPLE XV

N-(Gamma-aminopropyl)phenylundecylamine (20.0 grams, 0.065 mole) in isopropanol (30 grams) was quaternized with methyl chloride at 75°–80°C/70–75 psig in 3 hours in the presence of sodium bicarbonate (16.4 grams, 0.195 mole) with periodic venting. The isopropanol solution of N,N,N',N',N'-pentamethyl-N-(phenylundecyl)trimethylenediammonium dichloride had the following analysis after filtration:

| | |
|---|---|
| Diquaternary | 41.0% |
| Free amine | 0.3% |
| Amine · HCl | Nil |

EXAMPLE XVI

A 250 ml three neck flask equipped with reflux condenser, thermometer, gas sparger and magnetic stirrer was charged with 33.3 grams (0.1 mole) of phenylstearyl alcohol. The alcohol was heated to about 100°C and dry hydrogen bromide gas was bubbled through the reaction mixture for 3 hours. The mixture was then poured into ice water, ether added and the ether solution washed with water until the washings were neutral. The ether solution was dried over anhydrous sodium sulfate and the ether stripped off under reduced pressure. The product, phenylstearyl bromide, was obtained in 92.3% crude mass yield (36.4 grams) as an oil. Infrared analysis showed little or no free alcohol remaining.

A solution of 15.8 grams (0.04 mole) of phenylstearyl bromide and 19.25 grams (0.32 mole) of ethylene diamine in 250 ml of ethanol was refluxed for 3 hours. The alcohol solvent was removed under reduced pressure and the resulting mixture separated into two layers. The lower layer was removed and 100 ml of water added to the top layer. The oily layer which then formed was dissolved in ether and washed free of residual ethylene diamine with water. The ether solution was dried over anhydrous sodium sulfate and the ether stripped off under reduced pressure to yield 13 grams (87% crude mass yield) of N-phenylstearyl ethylene diamine having the following analysis:

| | |
|---|---|
| Neutralization equivalent | 218 (calc'd 187) |
| Primary Amine | 45.0% |
| Secondary Amine | 40.7% |

A glass pressure bottle was charged with 10.5 grams (0.024 moles) N-phenylstearyl ethylene diamine as prepared above and about 10 grams (0.12 mole) of sodium bicarbonate in enough isopropanol to result in a 50% active amine solution. The reaction mixture was heated to 50°–60°C. and methyl chloride was added to 55–70 psig. The reaction mixture was maintained at 50°–60°C. and about 55–70 psig with periodic venting of carbon dioxide over about an 8 hour period. The crude product, consisting mainly of N,N,N',N',N'-pentamethyl-N-phenylstearyl ethylene diammonium dichloride, was obtained as an isopropanol solution and after filtration had the following analysis:

| | |
|---|---|
| Diquaternary | 69.3% |
| Free amine | 0.9% |
| Amine · HCl | 8.1% |

EXAMPLE XVII

Following the procedure of Example XVI a solution of 15.8 grams (0.04 mole) of phenylstearyl bromide and 37.2 grams (0.32 mole) of hexamethylene diamine in 400 ml of ethanol was refluxed for three hours. After the same recovery procedure 15.2 grams (88.4% crude mass yield) of N-phenylstearyl hexamethylene diamine was obtained having the following analysis:

| | |
|---|---|
| Neutralization Equivalent | 243 (calc'd 215) |
| Primary amine | 59.8% |
| Secondary amine | 28.4% |

Ten grams (0.022 mole) of N-phenylstearyl hexamethylene diamine as prepared above was quaternized following the procedure described in Example XVI resulting in the isopropanol solution of N,N,N',N',N'-pentamethyl-N-phenylstearyl hexamethylene diammonium dichloride having the following analysis:

| | |
|---|---|
| Diquaternary | 47.7% |
| Free amine | 8.3% |
| Amine · HCl | Nil |

EXAMPLE XVIII

A solution of 2.3 grams of sodium bromide in 30cc isopropanol was added with stirring to a solution of 11.0 grams of N-9(10)phenylstearyl N,N,N',N',N'-pentamethyl trimethylene diammonium dichloride (1.84 milliequivalents/gram) in 100cc isopropanol. Less than 1cc of water was added to improve solubility. A white precipitate of sodium chloride formed immediately and was separated by filtration. Isopropanol was removed from the product by distillation under reduced pressure of about 10–20mm mercury to give the product, predominately, N-9(10)phenylstearyl N,N,N',N',N'-pentamethyl trimethylene diammonium dibromide having the following analysis by x-ray spectroscopy:

| | Percent | |
|---|---|---|
| Residual Chloride | 4.4 | |
| Bromide | 26.8 | (Theoretical 25.2) |

EXAMPLE XIX

A solution of 3.2 grams of sodium iodide in 30cc isopropanol was added with stirring to a solution of 10.5 grams of N-9(10)phenylstearyl N,N,N',N',N'-pentamethyl trimethylene diammonium dichloride (1.84 milliequivalents/gram) in 100cc isopropanol. A white precipitate of sodium chloride formed immediately and was separated by filtration. Isopropanol was removed from the product by distillation under reduced pressure of about 10–20mm mercury to give the product, predominately, N-9(10)phenylstearyl N,N,N',N',N'-pentamethyl trimethylene diammonium diiodide having the following analysis by x-ray spectroscopy:

| | Percent | |
|---|---|---|
| Residual Chloride | 3.6 | |
| Iodide | 26.5 | (Theoretical 34.6) |

EXAMPLE XX

A solution of 2.0 grams of sodium nitrate in 30cc isopropanol was added with stirring to a solution of 11.8 grams of N-9(10)phenylstearyl N,N,N',N',N'-pentamethyl trimethylene diammonium dichloride (1.84 milliequivalents/gram) in 100cc isopropanol. Less than 1cc of water was added to improve solubility. A white precipitate of sodium chloride formed immediately and was separated by filtration. Isopropanol was removed from the product by distillation under reduced pressure of about 10–20mm mercury to give the product, predominately, N-9(10)phenylstearyl N,N,N',N',N'-pentamethyl trimethylene diammonium dinitrate having the following analysis by x-ray spectroscopy:

|  | Percent |
|---|---|
| Residual Chloride | 4.5 |

EXAMPLE XXI

A solution of 1.0 grams of sodium hydorxide in 30cc isopropanol was added with stirring to a solution of 13.0 grams of N-9(10)phenylstearyl N,N,N',N',N'-pentamethyl trimethylene diammonium dichloride (1.84 milliequivalents/gram) in 100cc isopropanol. Less than 1cc of water was added to improve solubility. A white precipitate of sodium chloride formed immediately and was separated by filtration. Isopropanol was removed from the product by distillation under reduced pressure of about 10–20mm mercury to give the product, predominately, N-9(10)phenylstearyl N,N,N',N',N'-pentamethyl trimethylene diammonium dihydroxide having the following analysis by x-ray spectroscopy:

|  | Percent |
|---|---|
| Residual Chloride | 4.7 |

EXAMPLE XXII

A solution of 1.58 grams of sodium formate in 30cc isopropanol was added with stirring to a solution of 11.4 grams of N-9(10)phenylstearyl N,N,N',N',N'-pentamethyl trimethylene diammonium dichloride (1.84 milliequivalents/gram) in 100cc isopropanol. A white precipitate of sodium chloride formed immediately and was separated by filtration. Isopropanol was removed from the product by distillation under reduced pressure of about 10–20mm mercury to give the product, predominately, N-9(10)phenylstearyl N,N,N',N',N'-pentamethyl trimethylene diammonium diformate having the following analysis by x-ray spectroscopy:

|  | Percent |
|---|---|
| Residual Chloride | 4.8 |

EXAMPLE XXIII

The compounds of this invention have been found useful as emulsifiers in the formation of storage stable asphalt-in-water cationic emulsions. Lower chain length diquaternary ammonium salts having a phenyl group on the carbon atom alpha to a nitrogen atom do not function as asphalt emulsifiers.

In specific comparative tests 0.5% active diquaternary ammonium compound was mixed with 65% MC-3000 and 35% water, heated to 150°F and subjected to 5 minutes of high sheer by mixing with a blender at 1750 rpm. MC-3000 is a standard medium curing liquid asphalt made up of 85–100 pen. asphalt and a petroleum distillate solvent as described in the Asphalt Institute Specifications, Introduction to Asphalt, Manual Series No. 5, published by The Asphalt Institute, College Park, Md., 1962, page 58.

In one instance N-(1-phenylbutyl)-N,N,N',N',N'-pentamethyl trimethylene diammonium dibromide

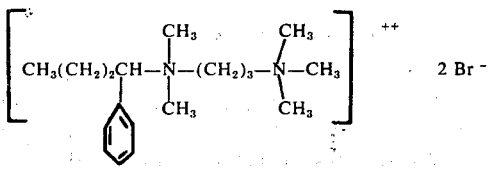

was used as the diquaternary ammonium compound. In this instance the formulation did not emulsify at all.

In the second instance a compound according to this invention, N-(phenyloctadecyl)-N,N,N',N',N'-pentamethyl trimethylene diammonium dichloride

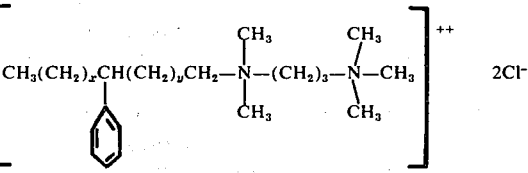

wherein $x$ is 0 to 14, $y$ is 1 to 15, and the total of $x$ and $y$ is 15, was used as the diquaternary ammonium compound. In this case, the asphalt emulsified in the water and the emulsion remained stable for more than a week.

While in the foregoing specification this invention has been described in relation to specific embodiments thereof and many details have been set forth for purpose of illustration, it will be apparent to those skilled in the art that the invention is susceptible to additional embodiments than those specifically disclosed herein, and that certain of the details as previously set forth can be varied without departing from the basic principles of the invention.

We claim:

1. Diquaternary ammonium compounds represented by the formula

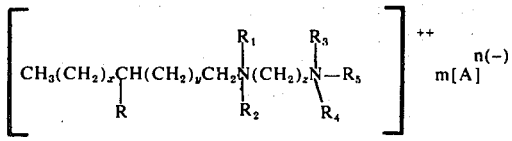

wherein $R_1$ and $R_5$ are selected from the group consisting of alkyl radicals having from 1 to 3 carbon atoms; $R_2$ is selected from the group consisting of alkyl radicals having from 1 to 3 carbon atoms, $-(CH_2CH_2O)_pH$, and

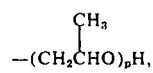

$R_3$ is selected from the group consisting of alkyl radicals having from 1 to 3 carbon atoms, $-(CH_2CH_2O)_wH$, and

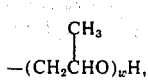

$R_4$ is selected from the group consisting of alkyl radicals having from 1 to 3 carbon atoms, $-(CH_2CH_2O)_rH$, and

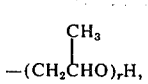

wherein $p$, $r$, and $w$ are integers from 1 to 40 and the sum of $p$, $r$, and $w$ is less than 80; R is selected from phenyl, naphthyl, and phenyl-substituted with from 1 to 2 groups selected from methyl, hydroxy, and methoxy; $x$ is an integer from 0 to 18, $y$ is an integer from 1 to 19, and the sum of $x$ and $y$ is an integer from 8 to 19; $z$ is an integer from 2 to 6; A is an anion; $m$ and $n$ are integers from 1 to 2 and the product of $m$ times $n$ is 2; said compounds consisting of isomeric mixtures with respect to the position of attachment of R to the alkyl chain.

2. The compounds of claim 1 wherein R is phenyl.
3. The compounds of claim 1 wherein $z$ is 2.
4. The compounds of claim 1 wherein $z$ is 3.
5. Diquaternary ammonium compounds of claim 1 represented by the formula

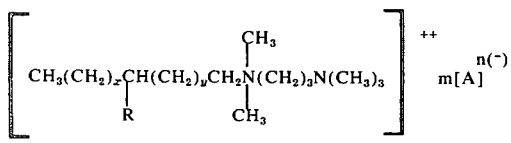

wherein $x$ is an integer from 0 to 14, $y$ is an integer from 1 to 15, the total of $x$ and $y$ is 15, A is an anion having a valence of 1 to 2, $m$ and $n$ are integers from 1 to 2 and the product of $m$ times $n$ is 2, and R is phenyl, said compounds consisting of isomeric mixtures with respect to the position of attachment of R to the alkyl chain.

6. Diquaternary ammonium compounds of claim 1 represented by the formula

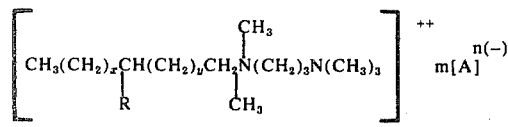

wherein $x$ is an integer from 0 to 14, $y$ is an integer from 1 to 15, the total of $x$ and $y$ is 15, A is an anion having a valence of 1 to 2, $m$ and $n$ are integers from 1 to 2 and the product of $m$ times $n$ is 2, and R is hydroxyphenyl, said compounds consisting of isomeric mixtures with respect to the position of attachment of R to the alkyl chain.

7. Diquaternary ammonium compounds of claim 1 represented by the formula

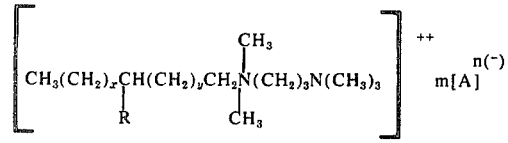

wherein $x$ is an integer from 0 to 14, $y$ is an integer from 1 to 15, the total of $x$ and $y$ is 15, A is an anion having a valence of 1 to 2, $m$ and $n$ are integers from 1 to 2 and the product of $m$ times $n$ is 2, and R is naphthyl, said compounds consisting of isomeric mixtures with respect to the position of attachment of R to the alkyl chain.

8. Diquaternary ammonium compounds of claim 1 represented by the formula

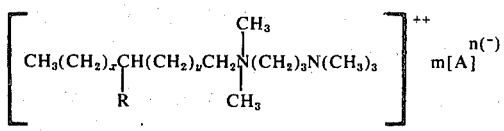

wherein $x$ is an integer from 0 to 14, $y$ is an integer from 1 to 15, the total of $x$ and $y$ is 15, A is an anion having a valence of 1 to 2, $m$ and $n$ are integers from 1 to 2 and the product of $m$ times $n$ is 2, and R is selected from phenyl, hydroxyphenyl, tolyl, naphthyl, anisyl, and xylyl, said compounds consisting of isomeric mixtures with respect to the position of attachment of R to the alkyl chain.

9. The compounds of claim 8 wherein A is chloride, $n$ is 1, and $m$ is 2.

10. Diquaternary ammonium compounds of claim 1 represented by the formula

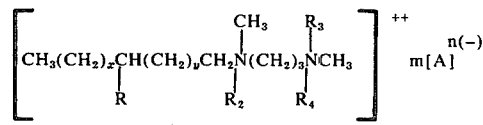

wherein $x$ is an integer from 0 to 18, $y$ is an integer from 1 to 19, the total of $x$ and $y$ is an integer from 8 to 19; A is an anion having a valence of 1 to 2, $m$ and $n$ are integers from 1 to 2 and the product of $m$ times $n$ is 2, $R_2$ is $-(CH_2CH_2O)_pH$, $R_3$ is $-(CH_2CH_2O)_rH$, and $R_4$ is $-(CH_2CH_2O)_wH$, with $p$, $r$, and $w$ being integers from 1 to 20 with the total of $p$, $r$, and $w$ not exceeding 50, and R is selected from phenyl, naphthyl and phenyl-substituted with from 1 to 2 groups selected from methyl, hydroxy, and methoxy, said compounds consisting of isomeric mixtures with respect to the position of attachment of R to the alkyl chain.

11. The compounds of claim 10 wherein A is chloride, $n$ is 1, and $m$ is 2.

12. Diquaternary ammonium compounds of claim 1 represented by the formula

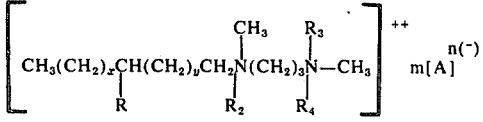

wherein $x$ is an integer from 0 to 18, $y$ is an integer from 1 to 19, the total of $x$ and $y$ is an integer from 8 to 19, A is an anion having a valence of 1 to 2, $m$ and $n$ are integers from 1 to 2 and the product of $m$ times $n$ is 2, $R_2$ is $-(CH_2CHO)_pH$, $R_3$ is $-(CH_2CHO)_rH$, and $R_4$ is $-(CH_2CHO)_wH$, (each with a $CH_3$ branch)

with $p$, $r$ and $w$ being integers from 1 to 20 and with the total of $p$, $r$ and $w$ not exceeding 50, and R is selected from phenyl, naphthyl, and phenyl-substituted with from 1 to 2 groups selected from methyl, hydroxy, and methoxy, said compounds consisting of isomeric mixtures with respect to the position of attachment of R to alkyl chain.

13. The compounds of claim 1 wherein the sum of $x$ and $y$ is 19.

14. The compounds of claim 1 wherein the sum of $x$ and $y$ is 8.

15. The compounds of claim 1 wherein A is selected from the group consisting of chloride, bromide, iodide, hydroxide, sulfate, nitrate, hydrochlorate, perchlorate, hypochlorate, formate and acetate.

16. The compounds of claim 1 wherein A is chloride.

17. Diquaternary ammonium compounds represented by the formula

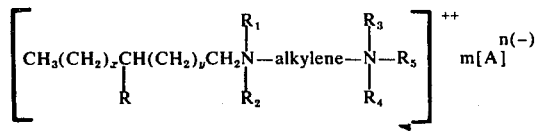

wherein $R_1$ and $R_5$ are selected from the group consisting of alkyl radicals having from 1 to 3 carbon atoms; $R_2$ is selected from the group consisting of alkyl radicals having from 1 to 3 carbon atoms, $-(CH_2CH_2O)_pH$, and

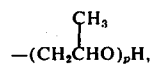

$R_3$ is selected from the group consisting of alkyl radicals having from 1 to 3 carbon atoms, $-(CH_2CH_2O)_wH$, and

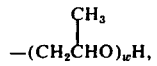

$R_4$ is selected from the group consisting of alkyl radicals having from 1 to 3 carbon atoms, $-(CH_2CH_2O)_rH$, and

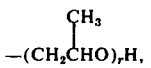

wherein $p$, $r$, and $w$ are integers from 1 to 40 and the sum of $p$, $r$, and $w$ is less than 80; R is selected from phenyl, naphthyl, and phenyl-substituted with from 1 to 2 groups selected from methyl, hydroxy, and methoxy; $x$ is an integer from 0 to 18, $y$ is an integer from 1 to 19, and the sum of $x$ and $y$ is an integer from 8 to 19; said alkylene group having 2 to 6 carbon atoms; A is an anion; $m$ and $n$ are integers from 1 to 2 and the product of $m$ times $n$ is 2; said compounds consisting of isomeric mixtures with respect to the position of attachment of R to the alkyl chain.

* * * * *